United States Patent [19]
Bailey et al.

[11] Patent Number: 5,432,093
[45] Date of Patent: Jul. 11, 1995

[54] SEQUENTIAL DEGRADATION OF PROTEINS AND PEPTIDES FROM THE N-TERMINUS

[75] Inventors: Jerome M. Bailey, Duarte; John E. Shively, Arcadia, both of Calif.

[73] Assignee: City of Hope, Duarte, Calif.

[21] Appl. No.: 256,540

[22] PCT Filed: Nov. 23, 1992

[86] PCT No.: PCT/US92/10048
§ 371 Date: Jul. 13, 1994
§ 102(e) Date: Jul. 13, 1994

[87] PCT Pub. No.: WO94/12538
PCT Pub. Date: Jun. 9, 1994

[51] Int. Cl.⁶ .................. G01N 33/68; C07K 1/107
[52] U.S. Cl. ........................... 436/89; 436/90; 436/92; 530/345; 530/402; 530/408

[58] Field of Search .............. 530/345, 402, 408; 436/89, 90

[56] References Cited

U.S. PATENT DOCUMENTS 5,008,205  4/1991  Horn ........................... 436/89

OTHER PUBLICATIONS

Aebersold et al, *Protein Science* 1: 494–503 (1992).
Pavlik et al, *Anal. Biochem* 201: 9–16 (1992).
Simpson et al, *Anal Biochem.* 177: 221–236 (1989).
Tsugita et al, *J. Biochem.* 106: 60–65 (1989).

*Primary Examiner*—Howard E. Schain
*Attorney, Agent, or Firm*—Edward S. Irons

[57] ABSTRACT

A novel method for the sequential degradation from the N-terminus of small samples of proteins or peptides. The released amino acids may be detected by mass spectrometry.

5 Claims, 2 Drawing Sheets

PTC - Peptide

TFA

ATZ - Amino Acid

PTH - Amino Acid

DMAP-TH - Amino Acid

SEQUENTIAL DEGRADATION OF PROTEINS AND PEPTIDES FROM THE N-TERMINUS

This invention was made with government support under Grant No. GM 46022 awarded by the National Institutes of Health. The government has certain rights in the invention.

FIELD OF INVENTION

This invention relates to the sequential degradation of proteins and peptides from the N-terminus. In particular, the invention permits N-terminal degradation of protein and peptide samples in the picomole to subpicomole range. The amino acid derivatives are rapidly detectable at high sensitivity by electrospray mass spectrometry.

BACKGROUND OF THE INVENTION

Proteins have a central role in all biological processes including the development and treatment of human disease. Recent advances make it possible to isolate proteins of biological interest which are present in tissues in subpicomole quantities. Study of the structure function aspects of these proteins requires sequence information prerequisite to cloning and expression thereof. There is a consequential need for improved methods to sequence proteins and protein fragments at sample levels several orders of magnitude smaller than is now possible.

Currently, protein sequence analysis is primarily accomplished with the use of an automated sequencer using chemistry developed by Edman over 40 years ago (Edman, 1950) (FIG. 1). Since that time improvement in the instrumentation has resulted in the ability to sequence smaller and smaller sample quantities (mmole to pmol), although the original chemistry has remained essentially unchanged. Current automated instrumentation permits 10–20 cycles of sequence determination of 10–50 pmol of sample (Simpson et al., 1989).

The major limitation of Edman chemistry is the approximately one picomole practical detection limit of the PTH amino acids. The current method involves separation of the phenylthiohydantoin (PTH) amino acids by high-performance liquid chromatography (HPLC) followed by UV detection.

Various proposals to increase the sensitivity of the PTH's by use of radiolabeled, chromophoric, or fluorescent isothiocyanate reagents have been described. 4-(N,N'-Dimethylamino)azobenzene-4'-isothiocyanate (DABITC), a highly chromophoric reagent, was introduced by Chang (Chang et al., 1976). Fluorescent reagents, such as fluorescein isothiocyanate (Maeda and Kawauchi, 1968; Muramoto et al. 1984), and dansyl-containing isothiocyanates (Hirano and Wittmann-Liebold, 1986; Hirano and Wittmann-Liebold, 1987; Jin et al., 1986; Jin et al., 1989; Salnikow et al. 1987) have also been evaluated as sensitivity enhancing reagents. Synthetic amino acid analogues prepared using these reagents have shown subpicomole sensitivity by HPLC analysis. However, the use of these reagents in automated sequencing has not surpassed the sensitivity of the standard Edman methodology. It is postulated that the large chromophore of these reagents interferes with the derivatization and cleavage reactions of the Edman degradation. Radiolabeled reagents undergo autoradiodegradation which results in decreasing product yields and increasing amounts of labeled by-products.

An alternative method involves treatment of the anilinothiazolinone (ATZ) derivative normally formed in Edman chemistry with a fluorescent amine (Tsugita et al., 1989). The advantage is that the derivatization and cleavage reactions of the Edman chemistry remain unchanged. Theoretically this chemistry should permit sequencing on femtomole levels of sample. However, investigation has revealed a number of problems rendering this chemistry of little value toward the goal of more sensitive sequencing. Foremost is the instability of the ATZ-amino acids which are required for reaction with the fluorescent amine. The ATZ-amino acids, in particular the hydrophilic amino acids such as histidine, glutamate, and aspartate, rearrange to the PTH derivative so rapidly that reaction with the fluorescent amine was not possible. A possible solution to this problem is to convert the PTH amino acid back to the ATZ amino acid so that reaction with the fluorescent amine will be possible.

The aminolysis of PTH amino acids is discussed in detail by Pavlik et al. (1992).

Replacement of the fluorescent amine with a reagent such as N,N-dimethylethylenediamine (DMED) has been found by applicants to permit detection in the femtomole level using electrospray mass spectrometry. The introduction of the tertiary amine to the amino acid derivative was found to enhance detection of the amino acid by 25 times as compared to the PTH-amino acid, thereby making mass spectrometry a viable method for enhancing the levels of detection during protein sequencing. However, the use of DMED requires reaction with the ATZ intermediate and therefore tends to suffer from the same problems as the fluorescent amine approach.

Recently a new reagent, 3-[4'(ethylene-N,N,N-trimethylamino)phenyl]-2-isothiocyanate has been introduced as a means of providing a thiohydantoin analogue with a quaternary amino group. (Aebersold et. al. (1992)) Although this reagent enhances detection of the released amino acid by mass spectral methods, it has a number of drawbacks. These include the synthesis of this reagent is complex, and the permanent positive charge makes this reagent polar and therefore requires the use of polar solvents to extract the amino acid derivatives. Such polar solvents cause sample washout thus limiting sequential yields. This problem necessitates covalent sample attachment with attendant poor yield therefore requiring larger amounts of sample and negating any potential benefit of enhanced sequencing capabilities. In addition, the large group used to attach the positive charge to the phenyl ring may have adverse affects on the kinetics of the sequencing chemistry. Dharmasiri, et al. synthesized Edman reagents having a pyridyl group as the basic site for enhanced detection of the TH amino acids which can be detected at the sub-femtomole level by electrospray mass spectrometry.

SUMMARY OF THE INVENTION

This invention provides a novel method for the N-terminal sequence determination of proteins and peptides. Pursuant to the invention, peptides may be sequenced at picomole and femtomole sample levels. Released amino acids may be identified by mass spectrometry, an inherently faster method of analysis than HPLC, thus permitting faster cycle times.

An important aspect of the invention involves the discovery that treatment of the ATZ derivative normally formed in Edman chemistry with a tertiary amine such as N,N-dimethylethylenediamine permits detection of the released amino acid in the subpicomole level using electrospray mass spectrometry. The method of the invention is ideally suited for automation using currently available commercial instrumentation. Sequences may be connected to an on-line preferably electrospray mass spectrometer.

A specific embodiment of the invention of particular significance entails the use as the derivatization reagent in the Edman cycle of an isothiocyanate which is a tertiary amine. Cleavage results in a tertiary amino-TH amino acid which may be detected by mass spectrometry. The tertiary amine reagent does not carry a positive charge during the organic extraction step, thus obviating the problem of sample washout which attends use of the quaternary amine reagent described by Aebersold. However, the tertiary amine reagent can be positively charged during the detection step by mass spectrometry to enhance the sensitivity of detection.

DETAILED DESCRIPTION OF THE INVENTION

The invention described with reference to FIG. 2: Pursuant to a preferred embodiment of the invention, the N-terminal amino acid of a peptide is derivatized with an isothiocyanate having a tertiary amine function.

The derivatized peptide is cleaved in known manner, e.g., with trifluoroacetic acid (TFA) to a PTH derivative having a tertiary amine function which is identified by mass spectrometry, preferably electrospray mass spectrometry. This derivative may be treated with base to increase its extraction into organic solvent without concomitant protein sample washout.

The amine isothiocyanate reagents having a tertiary amine function which are useful in this invention are represented by Formula I:

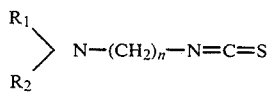

in which N is $R_1$ and $R_2$ are independently the same or different alkyl groups 1 to 15 carbon atoms in length or the same or different substituted or unsubstituted phenyl groups. $R_1$ and $R_2$ in combination may be $CH_2$ groups in a heterocyclic compound such as a pyridine. N is from 1 to 15.

The preferred reagent is dimethylaminopropyl isothiocyanate $(CH_3)_2N-(CH_2)_3-N=C=S$.

Figure 1:
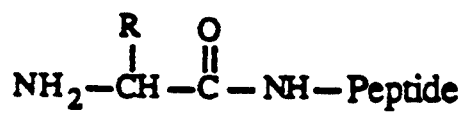
FIG. 1 illustrates the Edman N-terminal peptide sequencing chemistry.
Figure 1:
Figure 1:
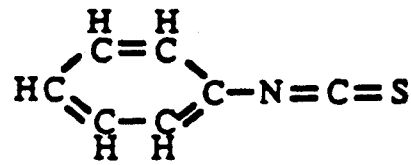
Figure 1:
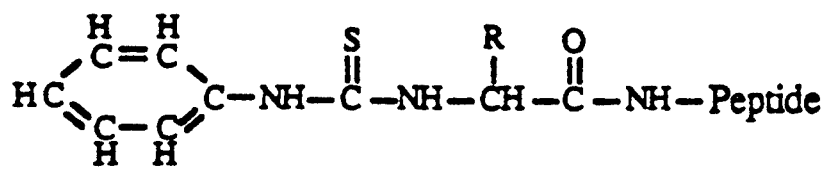
Figure 1:
Figure 1:
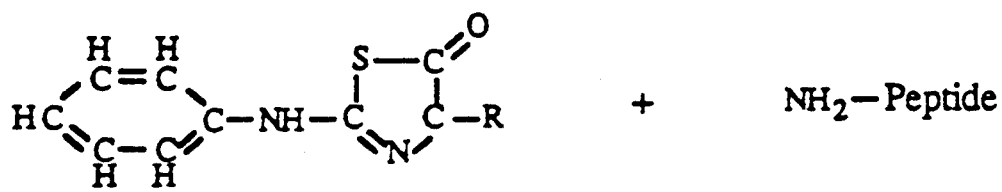
Figure 1:
Figure 1:
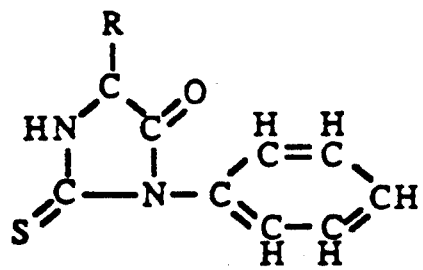
Figure 2:
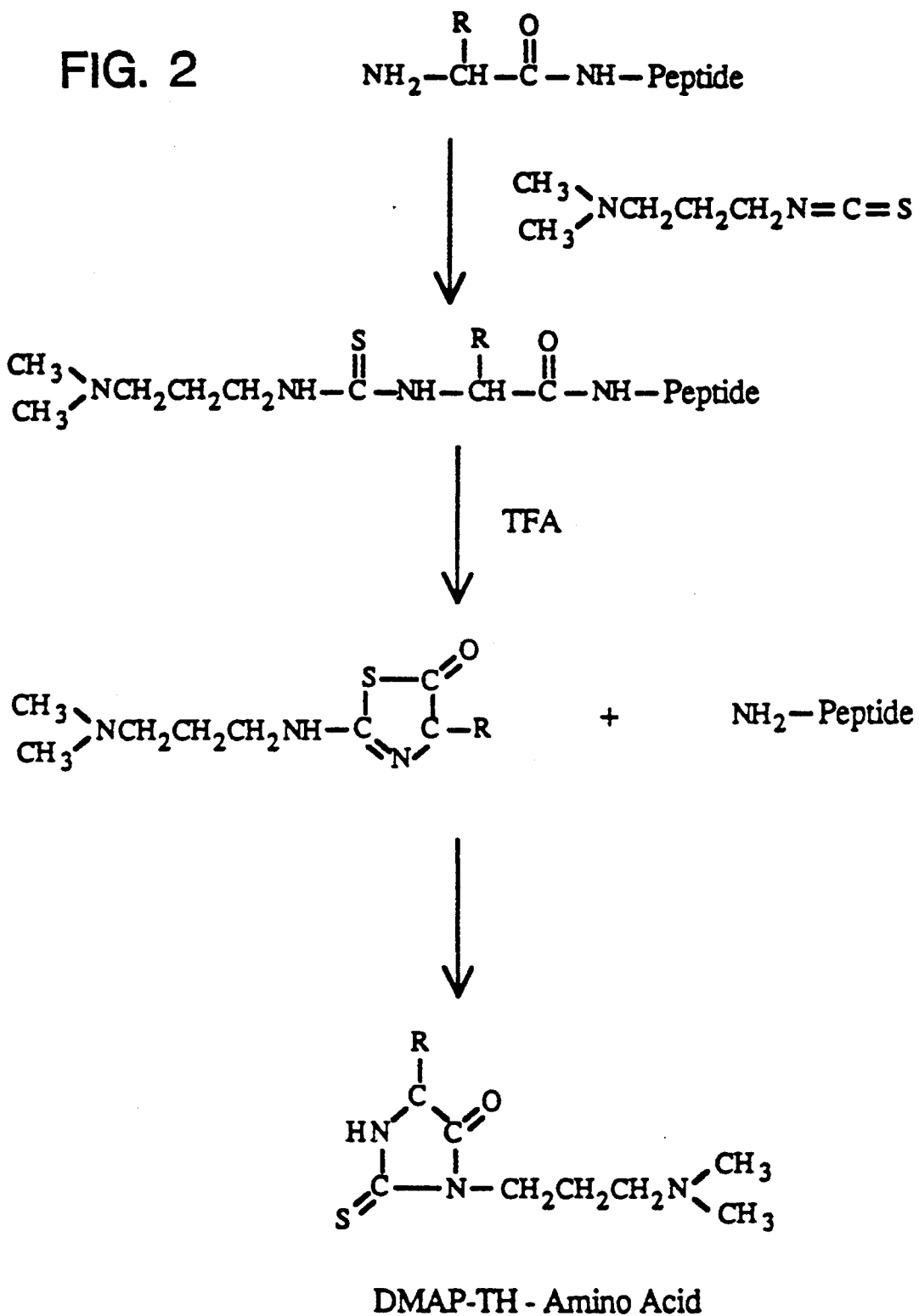
FIG. 2 illustrates a preferred embodiment of this invention.

FIG. 2 outlines the chemistry involved in the invention. The peptide/protein to be sequenced can be either covalently or non-covalently attached to various solid supports currently used in the field. Examples include PVDF, glass fiber filters, silica beads, polyethylene, carboxylated polyethylene, and polytetrafluoroethylene (Zitex). The sample is then treated with a liquid or gaseous solution of a tertiary amine such as triethylamine to convert the N-terminal amine to its unprotonated form. The peptide is then derivatized with dimethylaminopropyl isothiocyanate or similar reagent to form a peptidyl derivative. Isothiocyanate solvents known to be useful in such reactions may be used in proportions known to the art. Such solvents include anhydrous alkanols, preferably methanol which may contain from about 5% to about 50% alkanol. The cleavage reaction is then performed in conventional manner with liquid or gaseous trifluoroacetic acid or other acid such as hydrochloric acid. Trifluoroacetic acid is preferred.

Reagents such as dimethylaminopropyl isothiocyanate could be used to replace the phenyl isothiocyanate reagent currently used in commercial sequencers to produce the analogues (DMAP-TH-amino acids) shown in FIG. 2 instead of the PTH amino acids now formed in prior art.

This method for N-terminal sequencing has a number of advantages over the prior art. These include: (1) the simplicity of the chemistry, (2) the fact that reaction with the ATZ derivative is not required for introduction of the tertiary amine, (3) the preferred reagent is ideally suited for detection by mass spectrometry by virtue of its tertiary amine group. This eliminates the necessity for further chemical steps later in the sequence (after the washing step) in order to introduce the tertiary amine, thereby eliminating the possibility for introduction of unwanted background peaks due to excess amine reagent, (4) the derivatized amino acid product released during sequencing absorbs UV light at 269 nm with an extinction coefficient similar to the PTH amino acids released during the Edman degradation. This permits two modes of detection of the released amino acid: (i) standard UV detection, permitting equivalent sensitivity as prior art and (ii) detection by electrospray mass spectrometry, permitting rapid subpicomole detection, (5) use of mass spectrometry for detection of the released amino acids may permit faster cycle times. Current times range from 30 to 50 minutes and are determined by the length of time it takes to analyze the released amino acid by chromatography, and (6) the preferred reagent is commercially available, does not have a permanent positive charge, and does not possess a large bulky group which can adversely affect the sequencing kinetics.

EXEMPLIFICATION OF THE INVENTION

Reaction of Valine Methyl Ester With Dimethylaminopropyl Isothiocyanate

Valine ethyl ester (0.01 mol) in 30 ml of anhydrous methanol was reacted with dimethylaminopropyl isothiocyanate (0.01 mol) for 3 hours at 50° C. The solution was made basic by the addition of two equivalents of triethylamine. Solvent was removed by rotary evaporation. Water was added to the solid residue and the residue was filtered and washed with water. The residue was dissolved in methanol and analyzed by FAB/MS. The expected product, dimethylaminopropyl thiohydantoin valine (MH+ =244), was obtained.

Bibliography

Aebersold, R., et al. *Protein Science* 1:494–503 (1992)

Chang, J. Y., et al., *Biochem. J.* 153:607–611 (1986)

Dharmasiri, et al. The 40th Annual Conference on Mass Spectrometry and Allied Topics, p. 1791 (1992)

Edman, P. *Acta Chem. Scand.* 4:283–293 (1950)

Hirano, H., et al., *Biol. Chem. Hoppe-Seyler* 164:257–263 (1986)

Hirano, H., et al., In: Methods in Protein Sequence Analysis (Ed. B. Wittmann-Liebold) Springer-Verlag, Berlin, pp. 42–51 (1986)
Jin, S. W., et al. *FEBS Lett.* 198:150–154 (1986)
Jin, S. W., et al. In: Methods in Protein Sequence Analysis (Ed. B. Wittmann-Liebold) Springer-Verlag, Berlin, pp. 34–41 (1989)
Maeda, H., et al. *Biochem. Biophys. Res. Commun.* 31:188–192 (1986)
Muramoto, K., et al., *Anal. Biochem.* 141:446–450 (1984)
Pavlik, et al., *Anal. Biochem.* 201:9–16 (1992)
Salnikow, J., et al. In: Methods in Protein Sequence Analysis (Ed. K. A. Walsh) Humana Press, Clifton, N.J., pp. 247–260 (1987)
Simpson, R. J., et al. *Anal. Biochem.* 177:221–236 (1989)
Tsugita, A., et al., *J. Biochem.* 106:60–65 (1989)

We claim:

1. In a process for the sequential degradation of a protein or peptide from the N-terminus in which the N-terminal amino acid of a peptide is derivatized with an isothiocyanate and the derivatized N-terminal amino acid is cleaved to provide said derivatized N-terminal amino acid and a residual peptide, the improvement which comprises derivatizing said N-terminal amino acid of said protein or peptide with an isothiocyanate which has a tertiary amino function.

2. A process as defined by claim 1 in which said tertiary amino isothiocyanate has the formula

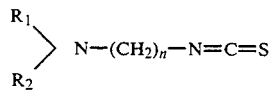

in which $R_1$ and $R_2$ are independently the same or different alkyl groups having 1 to 15 carbon atoms or phenyl groups or $CH_2$ groups in heterocyclic ring and n is 1 to 15.

3. A process as defined by claim 1 in which said N-terminal amino acid of said protein or peptide is derivatized with dimethylaminopropyl isothiocyanate.

4. A process for the sequential degradation of a protein or peptide from the N-terminus which comprises
   (i) providing a deprotonated sample of a protein or peptide to be sequentially degraded;
   (ii) derivatizing the n-terminal amino acid of said protein or peptide with dimethylaminopropyl isothiocyanate;
   (iii) cleaving said derivatized n-terminal amino acid from said protein or peptide to provide a separated dimethylaminopropyl thiohydantoin amino acid and a residual peptide having one less amino acid residue than said sample; and
   (iv) identifying said separated dimethylaminopropyl amino acid by mass spectrometry.

5. A process for the rapid sequential n-terminal degradation of a protein or a peptide and analysis of the degradation products which comprises providing an automated n-terminal sequencer connected on line to an electrospray mass spectrometer;

subjecting a deprotonated sample of a protein or peptide to derivatization and cleavage by said automated n-terminal sequencer;

said derivatization being accomplished by reaction of said sample with dimethylamino propyl isothiocyanate;

said cleavage providing a separated dimethylaminopropyl thiohydantoin cleavage product;

introducing said cleavage product directly into said electron spray mass spectrometer to identify said cleavage product.

* * * * *